(12) United States Patent
Landingham

(10) Patent No.: US 7,879,285 B2
(45) Date of Patent: Feb. 1, 2011

(54) PROCESS FOR FABRICATION OF CERMETS

(75) Inventor: Richard L. Landingham, Livermore, CA (US)

(73) Assignee: Lawrence Livermore National Security, LLC, Livermore, CA (US)

(*) Notice: Subject to any disclaimer, the term of this patent is extended or adjusted under 35 U.S.C. 154(b) by 239 days.

(21) Appl. No.: 10/260,121

(22) Filed: Sep. 27, 2002

(65) Prior Publication Data

US 2003/0049149 A1 Mar. 13, 2003

Related U.S. Application Data

(62) Division of application No. 08/829,034, filed on Mar. 31, 1997, now abandoned.

(51) Int. Cl.
*C23C 32/00* (2006.01)
*A61F 2/28* (2006.01)
*B22F 7/00* (2006.01)

(52) U.S. Cl. .................. 419/10; 623/23.51; 501/89
(58) Field of Classification Search .................. 164/98; 264/662, 666; 419/27, 10; 623/23.51; 501/89
See application file for complete search history.

(56) References Cited

U.S. PATENT DOCUMENTS 3,026,210 A * 3/1962 Coble .................. 501/153
4,150,317 A * 4/1979 Laska et al. .................. 313/631
4,906,295 A * 3/1990 Miyamoto et al. ............ 75/239
5,041,248 A * 8/1991 Renlund et al. ................ 264/44
5,249,621 A * 10/1993 Aghajanian et al. ........... 164/97
5,296,419 A * 3/1994 White et al. ................ 501/96.4
5,458,705 A * 10/1995 Mazur et al. ................ 148/669
5,511,603 A * 4/1996 Brown et al. .................. 164/97
5,518,974 A * 5/1996 Krahn et al. ................ 501/127
5,624,505 A * 4/1997 Mazur et al. ................ 148/407
5,628,938 A * 5/1997 Sangeeta et al. .............. 264/28
5,676,907 A * 10/1997 Ritland et al. ............... 264/643
5,702,542 A * 12/1997 Brown et al. ................ 148/406
5,735,332 A * 4/1998 Ritland et al. ................ 164/98
6,025,065 A * 2/2000 Claussen et al. ......... 428/307.7

FOREIGN PATENT DOCUMENTS

GB 2148270 A * 5/1985

OTHER PUBLICATIONS

David R. Lide, ed., CRC Handbook of Chemistry and Physics Internet Version 2007 (87th Edition), <http://www.hbcpnetbase.com>.*

* cited by examiner

Primary Examiner—Roy King
Assistant Examiner—Jessee R. Roe
(74) Attorney, Agent, or Firm—John P. Wooldridge

(57) ABSTRACT

Cermet comprising ceramic and metal components and a molten metal infiltration method and process for fabrication thereof. The light weight cermets having improved porosity, strength, durability, toughness, elasticity fabricated from presintered ceramic powder infiltrated with a molten metal or metal alloy. Alumina titanium cermets biocompatible with the human body suitable for bone and joint replacements.

13 Claims, 2 Drawing Sheets

PROCESS FOR FABRICATION OF CERMETS

CROSS-REFERENCE TO RELATED APPLICATION

This application is a divisional of application Ser. No. 08/829,034 filed on Mar. 31, 1997 entitled "Novel Cermets and Molten Metal Infiltration Method and Process for Their Fabrication", now abandoned.

The United States Government has rights in this invention pursuant to Contract No. W-7405-ENG-48 between the U.S. Department of Energy and the University of California, for the operation of Lawrence Livermore National Laboratory.

BACKGROUND OF THE INVENTION

1. Field of Invention

This invention concerns novel cermet materials comprising ceramic and metal components and a molten metal infiltration method and process for fabrication thereof. The cermets of the invention are fabricated from preformed ceramic powder infiltrated with a molten metal or metal alloy. The novel cermets are useful for a wide range of applications such as manufacture of surgical instruments, cutting tools, engine parts, wear parts, etc. Their properties, such as strength, durability, toughness, elasticity, etc. can be designed according to their intended use.

Additionally, the invention concerns cermets, particularly alumina-titanium cermets, having properties similar to bone. These cermets are made of components biocompatible with the human body and are suitable for bone and joint replacements.

2. Background Art and Related Disclosures

While the material technology has substantially advanced in recent years, providing many choices of materials having specific properties, there is still a need for materials having selected properties specifically suitable for specific purposes. These materials typically need to be durable, hard to break, non-fragile, non-brittle and yet elastic and reasonably light in weight. Additionally, their fabrication should be economically feasible and not overly laborious. Moreover, in order to meet requirements for their specific use, many of these materials need to be able to be custom designed.

Thus, it would be advantageous to have available a material having all above named properties and a process for fabrication of any such material where these properties could be easily varied and changed depending on used components and process conditions and design.

One example of the needed material having specific properties is the material having weight, structure, strength and other properties similar to and resembling bones or joints, which material would be suitable for bone or joints replacement.

Medical advances of past several decades have substantially extended life of the human population. The aging population, however, faces a multiplicity of disorders which may limit its quality of life. Among those disorders are osteoporosis, Paget's disease of bone and joints, and arthritis. All these disorders may cause limited mobility and often, particularly in the elderly, can result in death due to resulting bone fractures. When not fatal, these disorders still often require surgical bone or joint replacement of hips, knees, elbows, etc.

The major problem associated with the bone replacement is a lack of a suitable material which would have the same or similar properties as bone but that would also be compatible with the human body. The properties which the bone or joint replacement material need to possess include light weight, porosity, strength, durability, elasticity and, in order to prevent wear in joint areas and to prevent or allow tissue attachment in other areas, as need be, a possibility to be surface finished. Therefore, such material must have approximately the same porosity, weight and structure and must not be more fragile or more brittle than the normal bone.

Currently, several materials are known and medically acceptable as implants. While these materials, namely alumina ceramic ($Al_2O_3$) and titanium alloys containing 5% titanium and 4% aluminum (Ti5-4) or 6% titanium and 4% aluminum (Ti6-4), are acceptable as implant materials, alone or in combination, neither has the desired properties to replace bone or joints.

Thus, it would be advantageous to provide a biocompatible material which would have the strength, durability, elasticity and surface finish similar to the natural bone and which could also be custom shaped in a relatively short time so that surgeons could make necessary adjustments to the implant during the operation in order to properly fit the patient.

Ceramic/metal combination materials, known as cermets, are known. These cermets possess useful properties, such as toughness and strength, and have been used for manufacturing lightweight personnel armor, structural materials, cutting tools, radiation resistant structures, insulation materials, impact, abrasive and wear resistant structures, etc. However, none of the known cermets possess properties which would make them suitable for bone or joint replacement or for manufacture of other products requiring the similar properties as bone implants. This is due to the fact that the known processes for their preparation do not prevent ceramic powder particles shrinking, enlargement or cluster formation during their fabrication. These changes in particle sizes of the ceramic powder result in an uneven and unpredictable porosity of the resulting material.

A method for forming metal-filled ceramics is described in U.S. Pat. No. 3,718,441. Cermets which are boron-carbide-aluminum or boron-carbide-reactive metal composites are described in U.S. Pat. No. 4,605,440 and infiltration processing of boron carbide, boron and boride-reactive metal cermets is described in U.S. Pat. No. 4,718,941. Cermets prepared by combustion synthesis and metal infiltration are described in the U.S. Pat. No. 4,988,645. However, none of the above produced cermets possess specific properties as described above required for bone replacement or manufacture of other products. This is primarily due to methods and/or materials and conditions used for their fabrication.

There are two other methods currently known and used for fabricating cermets. The first method involves cold press and sintering (CPS). The second method involves hot pressing (HP) or hot isostatic pressing (HIP).

Cermets, such as cermets prepared from titanium-aluminum oxide (Ti-$Al_2O_3$) components, were prepared by the conventional process of cold pressing and sintering of the blended titanium (Ti) and aluminum oxide ($Al_2O_3$) powders. Typically, the blended titanium-aluminum oxide powders are formed into the desired shape, and submitted to a temperature at least as high as the sintering temperature of the titanium-aluminum oxide blend. This leads to a large shrinkage of more than 15% of the aluminum oxide particles. Additionally, these shrunk particle result in a grain growth and cluster formation of aluminum oxide particles occurs. The high sintering temperature to which these blends are submitted results in formation of a cermet containing dense aluminum oxide areas unevenly distributed throughout the matrix cermet interspersed with titanium filling-in voids between these unevenly distributed areas. This is due to the aluminum oxide particles sintering together into grains and clusters when submitted to the high sintering temperatures allowing the titanium migration only into the void sites between the growing grains of aluminum oxide clusters.

The growth of aluminum oxide particles into grains and clusters, therefore, does not allow an even distribution of the molten titanium within the sintered ceramic particles but rather results in molten titanium getting into voids between aluminum oxide grains and forming larger metal areas.

The cold pressing and sintering method thus results in cermets consisting of ceramic grains and clusters larger than 80 microns interspaced with unevenly distributed titanium areas larger than the titanium powder particle size used in the starting powder blend. Titanium thus forms distinct titanium islands within grains and clusters of the aluminum oxide matrix. Because of this uneven distribution due to the coarse dispersion of large titanium areas in a coarse structure of aluminum oxide grains, the mechanical properties of the formed cermets are poor and typically these cermets are fragile, brittle and their porosity and weight is uneven.

The cermets produced by cold sintering are not suitable for preparation of cermet materials which require that the material is light, tough, durable non-fragile or non-brittle and has a uniform porosity. These cermets do not have even distribution of titanium within the aluminum oxide matrix and are, therefore, fragile and subject to easy fracture. The shrinkage and grain growth occurring during the cold pressing and sintering are clearly not acceptable for bone replacement implant material which need to have a consistently porous microstructure strengthened with metal.

Some improvement on this microstructure was achieved by development of two subsequent methods utilizing the pressure during the sintering, namely hot pressing (HP) or isostatic hot pressing (HIP). This improvement consist of sintering of compositions of titanium in aluminum oxide (5 to 60 vol/%) at lower temperatures (1400-1600° C.) and by applying pressure to the powder preform while at these lower temperatures to force entry of titanium in between the aluminum oxide grains.

Hot pressing of the titanium-aluminum oxide powder blend is accomplished generally in a graphite die and punch assembly where the pressure is applied to the powder inside the dies through hydraulic force on the punches. The powders are heated to the desired densification temperature (1400-1600° C.) and the applied pressure assists in the rapid (<1 hour) densification of the powder.

Hot isostatic pressing is achieved by sealing the powder blend in a metal, such as, for example, molybdenum, or in a glass container and applying a gas pressure, generally argon or helium, to the outside of this container while heating the gas to the desired sintering temperature (1300-1500° C.).

The cermet products obtained by hot pressing or hot isostatic pressing have similar properties. Unfortunately, both these methods still result in the shrinkage and in the grain growth of the aluminum oxide-titanium powder blend and in an uneven distribution of the metal through the aluminum oxide. This is due to the same sintering problems observed during cold pressing and sintering, where the sintering is performed at lower temperatures and the process takes a longer time. Hot pressing or hot isostatic pressing take shorter time as they are performed under high pressure. Thus, while finer microstructures than those obtained during the cold pressing and sintering were obtained from hot pressing or hot isostatic pressing, such processing did not result in cermets having properties required for bone replacement. Even under relatively high pressure (<30,000 psi) conditions, the sintering process resulted in the growth of the titanium and aluminum oxide grains larger than 60 microns and in large shrinkage to achieve densification needed for bone replacement implant.

Therefore, the hot pressing improvement of the cold pressing and sintering process still does not provide material having a uniform distribution of metal throughout the ceramic matrix suitable for bone replacement or for manufacture of other products having similar requirements for material properties.

In an attempt to reduce the grain growth, special processing of the ceramic metal blend was suggested using coating the aluminum oxide particles with titanium metal. This was expected to allow the HP or HIP processes to achieve densification of the powder at lower temperatures and reduce grain growth. However, in order to be able to be coated with sufficient titanium metal and still achieve a dense product during hot pressing or hot isostatic pressing, the aluminum oxide particles must be larger than 40 microns. This limit prevents fabrication of cermets which would have no shrinkage, and would have uniform distribution of the metal within the aluminum oxide matrix assuring the strength, toughness and non-fragility of the bone replacement implant.

Thus it would be very advantageous to have available a material which would posses the above listed undesirable property and a method and process for its preparation eliminating the above listed disadvantages and problems.

It is therefore a primary objective of this invention to provide a cermet of which properties can be designed to specifically meet the requirements for its intended use. Due to the improved processing, the new cermet is light, has an even porosity, is strong, durable, elastic, and tough as well as non-fragile or non-brittle. The new cermet can be prefabricated into a near-net ceramic shape of the article to be used, and molten-metal-infiltrated after the final shaping. Additionally, the surface of the article can be surface finished in such a way that it fits its use. The new cermet which can be made of components fully compatible with the human body has properties similar to bone and is able to withstand the pressures and weight to which the bone in the body is constantly submitted without breaking. Additionally, it can be made to fit the patient bones and joints and surface finished to meet physiological functions of the replacement, such as tissue attachment, lubrication, etc.

All patents, patent applications, and publications cited herein are hereby incorporated by reference.

SUMMARY

One aspect of this invention is a new cermet comprising of a ceramic powder presintered into a porous ceramic matrix and infiltrated with a molten metal or metal alloy.

Another aspect of this invention is a cermet having properties custom designed for its intended use.

Still yet another aspect of the current invention is a cermet fabricated from a presintered ceramic powder selected from the group consisting of aluminum oxide, zirconium oxide, hafnium oxide, vanadium oxide, or combination of these ceramic powders and infiltrated with a molten metal such as titanium, aluminum, magnesium, nickel, lithium or calcium or alloys of these metals.

Still yet another aspect of this invention is a cermet fabricated from a ceramic selected from the group consisting of aluminum, zirconium, hafnium and vanadium nitride, boride, or silicate.

Yet another aspect of this invention is a method and a process for fabricating cermets of the invention by presintering and molten-metal-infiltration.

Another aspect of this invention is a new cermet which has an evenly distributed porosity and light weight and is strong, tough, durable, elastic, non-fragile and non-brittle.

Still yet another aspect of this invention is a cermet comprising a porous ceramic matrix fabricated by presintering ceramic powder of the same particle size limited to from about 10 to about 50 μ, at a sintering temperature which is higher than the melting point of the infiltrating metal and during sintering does not result in shrinkage, grain growth and a formation of voids, and by uniformly infiltrating the presintered ceramic matrix with a molten metal or a metal alloy.

Still another aspect of the current invention is a new cermet comprising a ceramic powder or a blend of ceramic powders presintered into a porous ceramic matrix having a zero or a very low wetting angle allowing quick and even molten metal infiltration along the surface and into the porous ceramic matrix.

Another aspect of this invention is a cermet suitable for manufacturing products such as surgical instruments, cutting tools, wear parts, engine components or implants for bone replacement.

Still yet another aspect of the current invention is a biocompatible titanium-aluminum oxide cermet material prefabricated as an aluminum oxide near-net shape preform of the article to be fabricated wherein said preform is custom finished by polishing, grinding and/or machining to fit its intended use and subsequently strengthened by an uniform infiltration of molten metal into a porous ceramic matrix.

Another aspect of the current invention is a cermet bone implant fabricated from a densely packed aluminum oxide ceramic by presintering said densely packed ceramic powder having the same particle sizes from about 10 to about 50 μ in a near-net shape of bone preform matrix at a sintering temperature higher than the melting point of infiltrating metal or metal alloy, said sintering temperature preventing shrinkage, grain growth and formation of intraparticle voids, said presintered ceramic matrix having a zero or very low wetting angle, and uniformly infiltrating a molten titanium or titanium containing alloy into said matrix.

Still yet another aspect of the current invention is a biocompatible titanium-aluminum oxide cermet prefabricated in near-net shape matrix preform of the bone or joint to be replaced wherein said preform is custom finished by polishing, grinding and/or machining to fit the patient's bone or joint, and subsequently strengthened by an uniform infiltration of molten metal into a porous ceramic matrix.

Definitions

As used herein:

"Cermet" means a material comprising a metal or a metal alloy and a ceramic powder or a mixture of ceramic powders. Cermet is fabricated from the ceramic powder selected from a group of compounds represented and exemplarized by the titanium-aluminum oxide system. Other systems, such as and including zirconium, hafnium, beryllium, vanadium oxides, nitrates, silicates or borides, etc., in combination with a metal, such as titanium, aluminum, magnesium, nickel, lithium, calcium, or their alloys are equally suitable for fabrication of cermets of the invention. In addition to these named systems, any other suitable alloy system meeting general conditions for processing of the cermets of the invention may also be advantageously used to fabricate these cermets using the molten-metal-infiltration method and process and are intended to be within the scope of the invention.

"Preform" means a cermet material prefabricated in near-net shape preform of the article to be molten infiltrated. Preform may be custom finished by polishing, grinding, machining, etc., to fit its intended use.

"Molten metal infiltration" means a method wherein the molten metal or an alloy is infiltrated into a porous ceramic matrix formed by presintering of the aluminum oxide or other ceramic powder under temperatures which are higher than the melting point temperature of the infiltrating metal and wherein the infiltration is typically performed under a protective environment such as under vacuum, or in argon, helium, hydrogen or nitrogen atmosphere.

"Alloy" means a combination of two or more metals. Such combination changes the properties, such as melting point, of the infiltrating metals.

"Uniform metal infiltration" means a metal evenly distributed within the porous ceramic matrix of the prefabricate.

"Sintering" or "presintering" means fusing ceramic powder particles into a bonded mass using heating at a temperature above the melting point of the infiltrating metal or metal alloy and optionally a pressure.

"Densification" means increasing density of the ceramic powder by pressure and/or sintering.

"Wetting angle" means a contact angle as defined and described in *J. Am. Ceramic Soc.*, 54:332 (1971). The wetting angle is measured in a sessile drop unit.

"Wetting" means any process in which an interface between solid phase and liquid phase is formed. When the two phases interface, these two phases are not in chemical equilibrium. During these non-equilibrium conditions, the interfacial energies and contact angle are continuously changing. This process continues until the system reaches a state of chemical equilibrium. The wetting phenomenon can be expressed as a contact or wetting angle measurement.

"Void" means empty areas and spaces unevenly distributed within the matrix formed of ceramic powder grains and clusters. The formation of these voids within the cermet matrix are undesirable as they contribute to the material's fragility and brittleness.

DETAILED DESCRIPTION OF THE INVENTION

Figure 1:
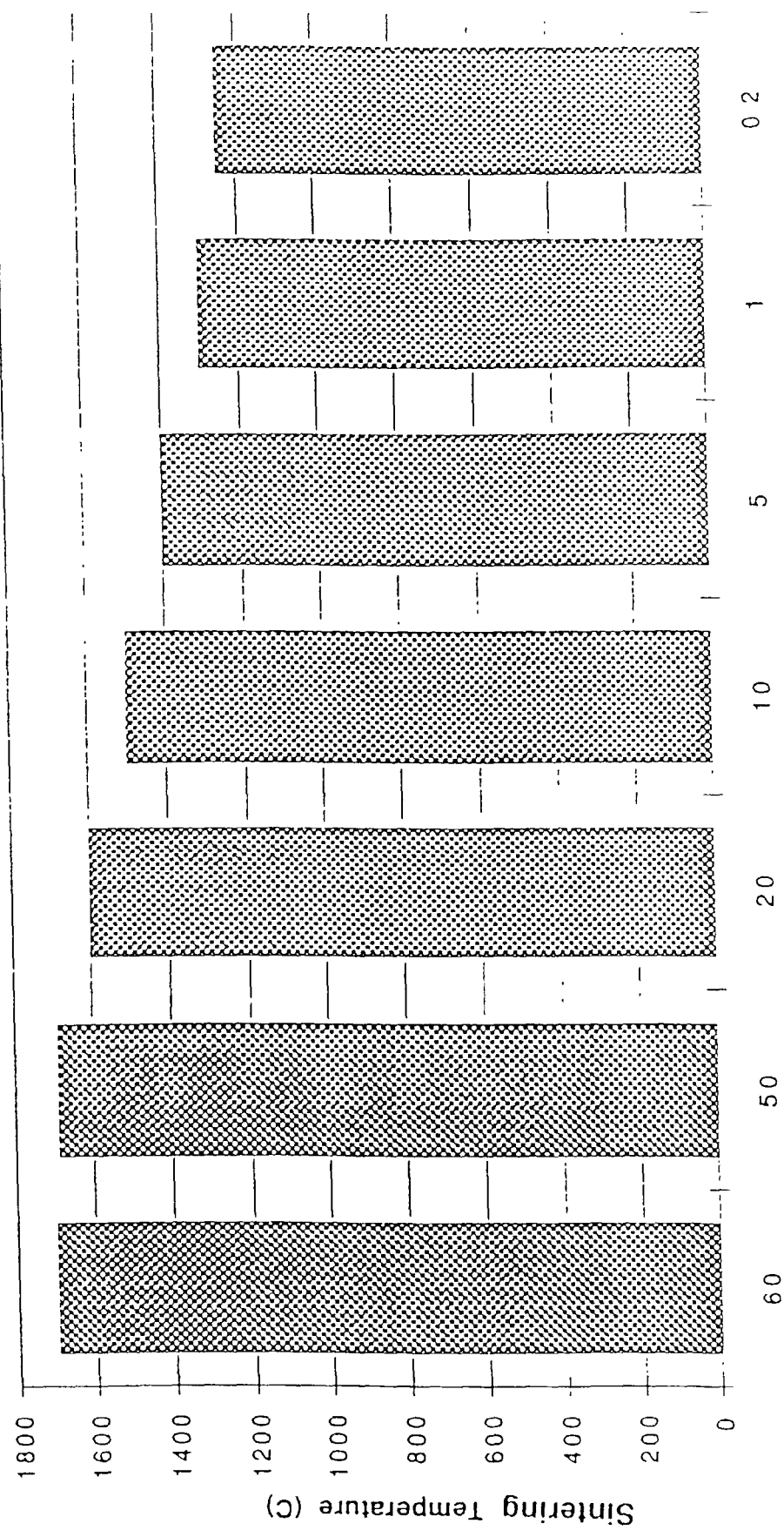
FIG. 1 is a comparative graph showing the effect of increasing the aluminum oxide particle size on its lowest sintering temperature.

This invention concerns novel cermet materials of which properties such as weight, porosity, strength, toughness, flexibility and elasticity can be custom designed for the intended use or for the use of the intended manufactured product. The new cermets are light in weight, durable, strong, tough, non-fragile and non-brittle and can be made of biocompatible components with human or animal body and are, therefore, suitable for manufacture of bone replacement implants, surgical instruments, cutting tools, wear parts, engine components, etc. The invention also concerns a method and a process for preparation of these cermets.

The new cermet material is a mixture of a ceramic, such as for example, aluminum oxide, zirconium oxide, hafnium oxide, beryllium oxide, vanadium oxide, boron carbide, aluminum nitride, zirconium nitride, hafnium nitride, vanadium nitride, aluminum boride, zirconium boride, hafnium boride, vanadium boride, aluminum silicate, zirconium silicate, hafnium silicate, vanadium silicate powders or their mixtures, in combination with a metal such as titanium, aluminum, magnesium, nickel, lithium, calcium, or other suitable metals, or their alloys, etc.

Briefly, the cermet of the invention is fabricated in a two-step process from a ceramic powder and from an appropriate metal or metal alloy.

The first step of the process provides a porous ceramic matrix formed of the preformed ceramic powder. Due to a novel process for preparation of these cermets, the sizes of the ceramic powder particles are stable, do not shrink or grow into large grains or clusters after preforming. When submitted to infiltration with the molten metal or alloy, the preform remains the same as the initial preform because there is little or no shrinkage.

The stability of the ceramic preformed powder is one of the novel aspects of the invention distinguishing the invention from the other known or previously described processes. All other processes, as discussed in the background section, result in ceramic powder particles growing during sintering into larger grains and clusters, in void formation, and in an uneven and uncontrollable porosity of the ceramics. This growth typically continues during the molten metal step. Thus, most of the previously described cermets result in ceramic-metal materials which are brittle and fragile, have unpredictable weight and metal enforcement and are in general unsuitable for fabrication of bone implants or other products of manufacture requiring the uniform distribution of the infiltrating metal through the porous ceramic matrix.

The second step of the process, namely a molten metal infiltration, allows an even and uniform infiltration of the uniform porous preform ceramic matrix with a molten metal or a suitable metal alloy under conditions which prevent further sintering of the ceramic preform or grains. The first process step thus involves partial sintering of the ceramic powder particles into the porous preform matrix having preferably a premolded shape of the intended product. This partial sintering results in a light fusion of ceramic powder particles at higher temperatures than those of the molten metal or alloy to be used for metal infiltration. During this latter step, the ceramic particle sizes remain stable. The processing pressure and difference between the temperature used for sintering in step one and temperature conditions used in step two for metal infiltration prevent the further particle growth during the molten metal infiltration. These conditions further assure that during the molten-metal-infiltration at lower temperatures than those used for ceramic powder sintering, the molten metal is evenly and uniformly distributed throughout the porous preform ceramic matrix. Because the ceramic matrix is made of the ceramic powder particles of the same size lightly sintered together, molten metal is easily infiltrated into this ceramic matrix.

The molten metal infiltration into the presintered ceramic matrixes under the process conditions of the invention, therefore, results in unexpectedly improved mechanical and physical properties such as high fracture toughness, increased strength and wear resistance making the cermets of the invention suitable for manufacturing products having specific requirements as to the weight, porosity, strength, durability, toughness, flexibility, elasticity and variability of design a surface finish of cermet products.

A primary advantage of the invention is that by changing the particle sizes of the ceramic powder, pressure and temperature conditions, and by selecting a suitable metal or metal alloy for metal infiltration, the properties of the resulting cermet can be easily designed, modified or changed. Two examples of cermets with widely variable properties are the system of (1) tungsten carbide-cobalt (WC—Co) and (2) titanium carbide molybdenum nickel (TiC—Mo—Ni) cermets. These cermets are used in the commercial field as various grades such as for example C-1, C-2, C-3, etc., depending on the amount of Co in the WC matrix containing 1% Co, 2% Co, 3% Co, etc., respectively. The higher the amount of Co content, the stronger and tougher the cermet, but at the expense of decreasing hardness and wear properties. The similar effect is observed for the TiC—Mo—Ni system. The application of such cermets determines which grade cermet is best for the intended purpose and illustrates versatility of the invention.

1. Ceramic Powder Matrix and Its Fabrication

The cermet of the invention typically comprises at least two major components, namely a ceramic and a metal or a metal alloy. Ceramic is a single ceramic powder or a mixture of several powders and the metal is a single metal or an alloy of two or more metals. Additionally, additives improving the properties of the cermet or the processing conditions may be optionally added to the ceramic powder or to the metal or metal alloy. Additives such as, for example, calcium oxide, magnesium oxide, sulfur or any such compound are added to the ceramic powder to reduce grain growth, shrinkage, cluster formation, etc., during sintering. Additives such as nickel, magnesium, calcium, aluminum, lithium and any such elements are added to a primary metal, such as for example titanium, to lower the melting point of the metal or alloy and in this way to lower molten metal infiltration temperature and increase wettability. Other additives, such as boron, carbon, nitrogen, silicon, etc., can also improve strength and other properties.

The first component of the cermet of this invention is a ceramic powder, preferably an oxide metal such as aluminum oxide, comprising spherical and/or smooth surface particles having a low surface area to retard sintering during the molten-metal-infiltration process. This powder is presintered into preforms having an evenly distributed porosity. Ceramic powder particles can be packed into a shape and fused at their contact points by controlling the temperature, pressure, and/or protective environment during sintering. The protective environment includes but is not limited to hydrogen, argon, helium, nitrogen atmosphere or vacuum, etc.

Typically, the preforming of the ceramic powder into a near-net shape is done by any process suitable therefor such as hydraulic pressing in a die, in a rubber or plastic mold, slip casting a slurry, extrusion pressing, injection molding, etc.

The atmosphere may, for example, include a vapor that assists the particle fusion as silicon oxide (SiO) or can deposit aluminum oxide at the surface of the aluminum oxide particles by a chemical vapor deposition process (CVD). CVD is accomplished by using aluminum chloride ($AlCl_4$) in moist hydrogen atmosphere according to the equation $AlCl_4 + H_2 + H_2O \rightarrow Al_2O_3 + HCl$. The $Al_2O_3$ particles are bonded with the CVD $Al_2O_3$ at their contact points.

The preforming or presintering step in the process for cermets fabrication is based on properties of the ceramic powder or a mixture of two or more ceramic powders. These properties include the size of the ceramic powder particles, their surface, composition, and the sintering temperature.

Selecting the appropriate ceramic powder or the mixture of powders typically involves testing of the particle size vis-a-vis the powder's sintering temperature, as illustrated in FIG. 1. Subsequently to such testing, the ceramic powder or its mixture, its particle size and the temperature are selected which assure that following the presintering the ceramic particles remain of the same size, that they do not shrink, grow or form clusters and voids within the matrix.

In order to determine the optimal sizes of the ceramic particles as well as the temperature suitable for the ceramic matrix formation, the aluminum oxide particles of various sizes were submitted to sintering under increasing temperature. Results are seen in FIG. 1.

FIG. 1 shows the effect of increasing the aluminum oxide particle size on its initial sintering temperature. Particles having increased size have reduced surface area, and as seen in FIG. 1, these particles require higher sintering temperature. The sintering temperature of very small aluminum oxide particles between 0.2 and 1 µ was found to be around 1250-1300° C. The sintering temperature of aluminum oxide particles having sizes from 5 to 20 p was found to be from 1400° C. to 1600° C. These temperatures are below the melting point 1668° C. of titanium. Therefore, the aluminum oxide powder having the 5-20 µ particle sizes is not suitable to be presintered into the cermet matrix according to the invention unless the metal or metal alloy used for molten metal infiltration has the melting point lower than 1400° C. to 1600° C. temperature. The ceramic preform can be improved depending on the exact particle size and temperature used for sintering as well as on the presence of additives or impurities which retard shrinkage of the ceramic preform at the infiltration temperature.

According to the FIG. 1, the sintering temperature of aluminum oxide powder having particle sizes about 50 µ is about 1650° C., which is still below 1668° C. melting point of pure titanium. In this case, therefore, the pure titanium would not be suitable for molten metal infiltration unless combined with another metal into an alloy having the temperature lower than 1650° C. so that metal alloy of the metal combination would have a temperature lower than 1650° C. and would not cause aluminum oxide sintering.

The sintering temperature of particles above 50 µ is around 1700° C. which would fit within the general conditions of the method of the invention. These particles were found to have limited usefulness for preparation of the ceramic matrix according to the invention, as these particles would fuse together at 1700° C. When infiltrated at this temperature, their relatively large size would prevent shrinking and grain growth. This would result in an even and uniform distribution of the metal through the matrix having, however, relatively large microstructure.

When the ceramic powder or a blend of several powders contain naturally or artificially added additives or impurities, such as sulfur, calcium oxide, magnesium oxide, etc., in amounts between about 0.01 to about 1%, such small additions or presence of these impurities at the surface of the ceramic powder particles helps retard sintering and grain growth of smaller particles.

Although the actual size of the selected ceramic powder particles depends on the metal or metal alloy used, the preferred particle sizes of the ceramic powder used for formation of the ceramic porous matrix have particles between about 10 and 50 µ. The most preferred particles sizes for aluminum oxide powder are about 10 µ. At this size, and at about $10^{-6}$ torr pressure, the sintering temperature is around 1500° C.

In practice, when the appropriate combination of a ceramic powder with a selected metal or metal alloy is contemplated, ceramic powders suitable for preparation of cermets of the invention selected from the group consisting of aluminum, zirconium, hafnium, beryllium or vanadium of oxides, carbides, nitrates, silicates, borides, etc., or their mixture are submitted to testing and their individual sintering temperature is determined as described in Example 1. The density of each compacted ceramic matrix is measured and its sintering temperature is determined. The preferred density of the ceramic matrix is about 50 to about 70, most preferably about 60%. Preferred porosity of the ceramic matrix is about 30 to about 50, most preferably 40%. Because of their different physical and chemical properties, the sintering temperature for each individual ceramic powder or a mixture of two or more powders is different. However, the principle of determination of the optimal sintering temperature vis-a-vis the particle size is the same as for aluminum oxide described herein.

The powder particle size selected for each cermet is based on the sintering temperature of that particle size and such sintering temperature must be above the melting point of the selected metal or metal alloy used for molten metal infiltration.

Thus, when the cermet is designed, the suitable ceramic powder is selected, for example the one which is physiologically acceptable, then the sintering temperature of the various particle sizes of each ceramic powder or a blend of two or more powders is determined and then the most optimal particle size is selected depending on the melting point of the metal or the alloy selected to be used for infiltration.

The selected particles are then cast into their near-net shape, presintered at their sintering temperature into a desired shape prefabricate forming the stable porous ceramic matrix not subject to any significant sintering during the molten-metal-infiltration process. Significant sintering during the infiltration process would close off the connecting porous channels and infiltration would stop.

The density and porosity of the ceramic matrix is designed based on the intended use of the cermet.

2. A Molten Metal Infiltration Method

The cermets of the invention are preferably prepared by the molten-metal-infiltration method.

Previous attempts to use molten-metal-infiltration for other cermet systems have not been very successful, especially in the oxide-metal systems, because at molten metal temperatures it results in further sintering of the ceramic powder and the molten metal infiltration into the ceramic powder is hindered by the loss of interconnecting pores.

It has now been found that under proper conditions, molten metal can be infiltrated into a powder preform of metal carbide, metal oxide, metal nitride, metal boride, etc., and that under these conditions a fully dense ceramic/metal cermet is obtained.

As described above, the first condition for successful fabrication of the ceramic/metal cermet is the use of sintering temperature for presintering of the ceramic powder particles into the porous ceramic matrix which temperature is higher than the melting point of the infiltrating metal. The second condition is the molten metal infiltration at the infiltration temperature which is lower than the sintering temperature used in the first step. This prevents further sintering of the ceramic powder particles during the molten metal infiltration.

The lack of further sintering of ceramic particles allows the molten metal to "wet" the surfaces of the ceramic within the porous ceramic matrix and infiltrate into its porous structure. Such infiltration does not result in shrinkage to achieve densification, there is little to no sintering or grain growth of the ceramic particles since the infiltration temperature is lower than the sintering temperature of the ceramic powder. The high wetting ability of the molten metal at these lower temperatures allows rapid and uniform infiltration of the metal or metal alloy into the ceramic matrix in less than 30 minutes.

Under the normal circumstances and using previously known methods without current modifications and improvements according to the invention, the relatively high melting temperature (1668° C.) of titanium would prevent the infiltration of molten titanium into an aluminum oxide powder preform. This is because the infiltration temperature for the molten titanium is significantly higher than the sintering temperature of fine (10-50 u) aluminum oxide powder particles. Therefore, when the normal melting point temperature of titanium is used, the aluminum oxide particles sinter rapidly at this high (1668° C.) temperature, grow into the grains and seal off the open pores between the particles and in this way prevents the uniform molten titanium infiltration of the ceramic matrix.

In the molten metal infiltration step of the process, the second component, namely a light-weight metal, such as titanium, aluminum, manganese, nickel, calcium, lithium or their respective alloy, is infiltrated into the porous ceramic matrix at the temperature which is lower than the sintering temperature of the used ceramic powder.

In practice, the metal or metal alloy is selected according to its melting point temperature which must be lower than the sintering temperature of the used ceramic powder. The selected metal or metal alloy is melted at its melting point temperature and then, as a molten metal, is brought in contact with the porous ceramic matrix so that the metal wets the ceramic within the porous ceramic matrix. The metal must wet the ceramic to infiltrate into it or a pressure must be applied to the molten metal to force it into the porous ceramic matrix.

Wetting of the ceramics assists in the molten metal infiltration. In this respect, the wetting angle expressed in degrees is a measure of the ceramics/metal interface. The wetting angle of the molten metal depends on the ceramics, metal or metal alloy composition, on ceramic and metal interaction, on infiltration temperature, atmosphere, and pressure. The wetting angle decreases with increased temperature. For the best infiltration, the wetting angle is either zero or as close to zero ($\leq 200$) as possible. When the metal infiltration is performed at a temperature having the 180 degrees wetting angle, the metal stays at the point of infiltration and forms into spheres of molten metal. This would prevent even and uniform metal distribution throughout the whole ceramic matrix. When the metal is infiltrated at a temperature having a zero wetting angle, the metal spreads evenly throughout the ceramic matrix because the surface energy allows it to spread more easily.

Figure 2:
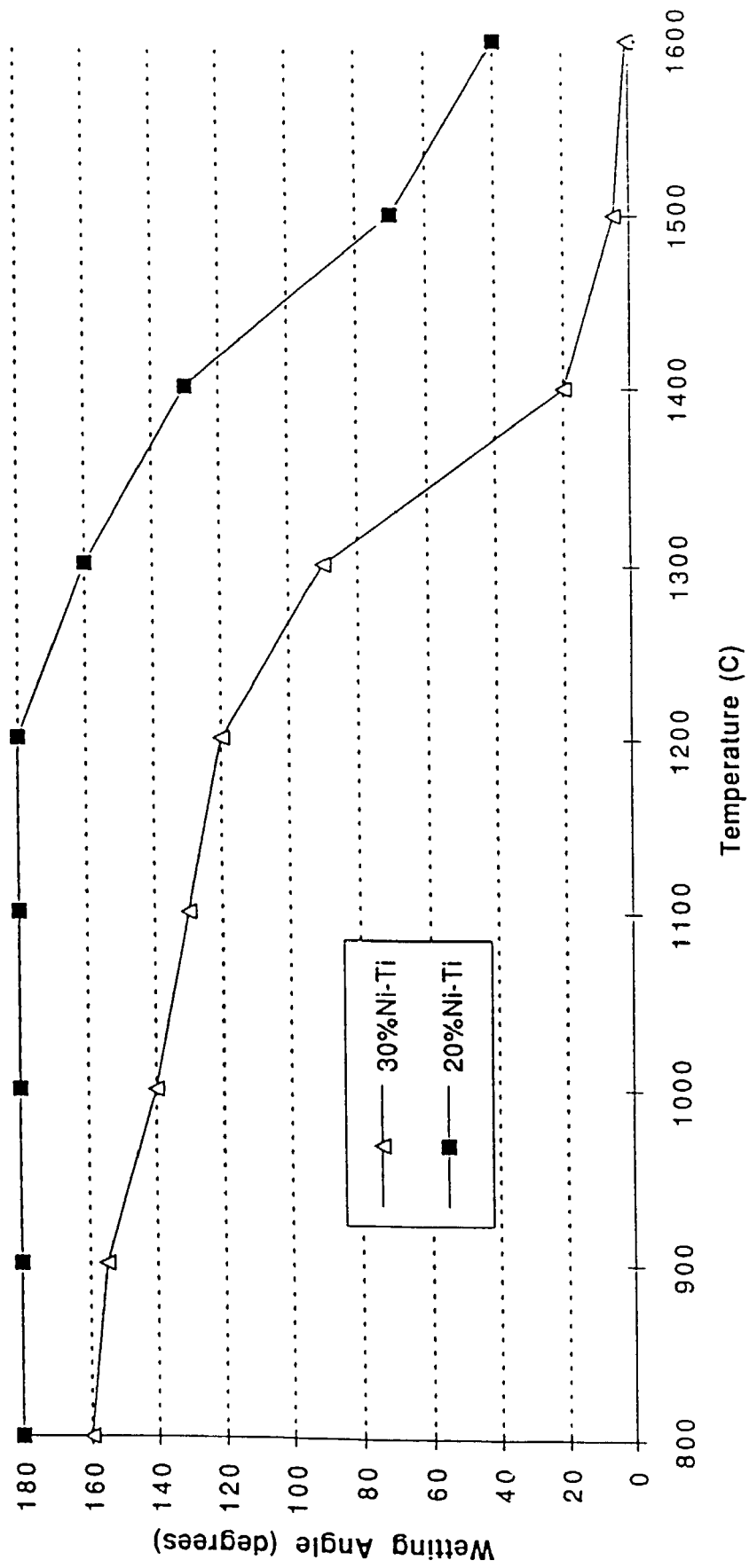
FIG. 2 is a graph showing improved wetting of an alloy consisting of titanium and nickel.

Dependence of the wetting angle on the temperature is illustrated in FIG. 2 for two Ti—Ni alloys.

According to the invention, metal infiltration can be either subsequent to the ceramic matrix formation or simultaneous with formation of the matrix provided that the simultaneous infiltration and matrix formation does not lead to the sintering and shrinkage of the ceramic powder.

For the cermets of the invention, a uniform distribution of the metal within the ceramic matrix is essential and necessary since only when the metal is uniformly distributed throughout the porous matrix, the cermet has properties required for bone replacement or for manufacturing products which require it to be evenly porous, light in weight, strong, tough, durable, elastic, non-fragile and non-brittle. The porosity in the ceramic matrix can be graded to give desired properties at various regions of the cermet component.

The molten-metal-infiltration of the invention is performed under as low temperature conditions as is possible in order to prevent the sintering of the ceramic powder particles into large grains or formation of clusters.

The ability of the metal, preferably titanium, to "wet" the surface of the ceramic, preferably aluminum oxide, is advantageously improved by substituting the metal with an alloy or by additions of one or more other metals or metal alloys prior to or during molten metal infiltration. In the case of titanium, addition of a metal, such as nickel, copper, iron, manganese, aluminum, silica, etc., in amounts of less than 45 weight percent lowers the melting point of titanium and increases its "wettability" onto aluminum oxide as seen in FIG. 2.

The suitable binary, ternary or quaternary metal alloys and their melting points are listed in Table 1.

TABLE 1

Titanium Alloys Melting Points
Binary, Ternary and Quaternary Alloys of Titanium (Ti)
With Melting Points Below Pure Ti (1668° C.)
Titanium Alloy Compositions

| Binary Alloys (Balance Ti) | Ternary Alloys (>60% Ti) | Melting Point (C.) | Quaternary Alloys (>60% Ti) | Melting Point (C.) |
|---|---|---|---|---|
| 40% Cu | | 990 | Mn—Cu—Si | 800 |
| 30% Ni | | 955 | Fe—Cu—Si | 1300 |
| 40% Al | | 1455 | Al—Cu—Mg | 500 |
| 25% Fe | | 1085 | Al—Fe—Si | 1200 |
| 15% Si | | 1330 | Al—Ni—Si | 1200 |
| 40% Mn | | 1250 | Fe—Ni—Si | 1200 |
| 25% Co | | 1025 | Al—Mn—Fe | 1150 |
| 10% Si | | 1330 | Al—Mo—Fe | 1200 |
| | 30% Cu—Co | 1400 | | |
| | 35% Mg—Cu | 552 | | |
| | 35% Mn—Cu | 870 | | |
| | 15% Si—Cu | 802 | | |
| | 20% Fe—Cu | 1450 | | |
| | 35% Al—Cu | 750 | | |
| | 35% Mg—Al | 450 | | |
| | 35% Al—Fe | 1165 | | |
| | 15% Al—Ni | 1385 | | |
| | 12% Si—Al | 577 | | |
| | 10% Si—Ni | 1152 | | |
| | 12% Si—Co | 1195 | | |
| | 20% Si—Fe | 1200 | | |
| | 30% Co—Fe | 1470 | | |
| | 20% Mn—Fe | 1450 | | |
| | 30% Mo—Fe | 1450 | | |
| | 20% Nb—Fe | 1360 | | |
| | 30% Ni—Fe | 1450 | | |
| | 15% Zr—Fe | 1330 | | |

Table 1 provides a list of exemplary binary, ternary, and quaternary titanium alloys that have melting points below the melting point of pure titanium (1668° C.).

As seen in Table 1, addition of 10 to 40% of a single metal to titanium to form binary alloys results in substantial lowering of the melting point below 1668° C. For example, addition of 40% copper to balance titanium decreased the melting point of this alloy to 990° C., addition of 10% of silica lowered the melting point of this binary alloy to 1330° C. Ternary alloys where the titanium is present in an amount higher than 60% decrease the melting points to about one-third of the melting point of the pure titanium. For example, addition of 35% of a manganese-copper mixture results in decrease of the melting point to 552° C. and a mixture of 35% of manganese-aluminum decreases the melting point to 450° C. Quaternary alloys, similarly, have lower melting points than pure titanium. All these alloys and their combinations as well as alloys formed with other metals are suitable for the infiltration of the ceramic matrix prepared by the method of this invention and all these combinations are intended to be within the scope of the invention.

When another metal or alloy thereof is selected to be used for fabrication of the cermets of this invention, the process illustrated in Table 1 is repeated, that is the melting points of the single metal and its binary, ternary and quaternary alloys are determined and matched with the selected ceramic powder so that the sintering temperature is higher then the melting point of the metal to be used.

The alloy of the invention which would be used for fabrication of the bone replacement implant preferably contains metal or metals which are approved for use in humans. As discussed above, the wetting of the ceramic with metal is desirable to obtain implant material for bone replacement. Therefore, before the cermet of the invention is fabricated, the wetting angle of the metal or alloy is also investigated and the temperature at which there is highest wetting (i.e. lowest wetting angle) is achieved. FIG. 2 shows improved wetting shown as decreasing wetting angle of two alloys, namely the alloy comprised of 30% nickel-titanium compared to 20% nickel-titanium alloy. As seen in FIG. 2, at increasing infiltration temperatures from 800° C. to 1600° C., the wetting angle of the alloy comprising increased amounts of nickel (30% Ni—Ti) was lower and had improved wetting compared to the alloy comprising only 20% of nickel (20% Ni—Ti). For the 20% Ni—Ti alloy, the wetting angle of 180 degrees was observed until the temperature reached 1200° C. Only after that temperature was reached, the wetting angle of this alloy begun to decrease. At a temperature of about 1600° C., the wetting angle of this alloy decreased to about 40 degrees. The 30% Ni—Ti alloy, on the other hand, has shown increased wettability, i.e., decreasing wetting angle constantly from 160 degrees at temperature 800° C. to about 20 degrees at temperature 1400° C. and zero wetting angle at temperature 1600° C., that is well under melting point of pure titanium. Thus, the wettability of the 30% Ni—Ti was substantially improved against wettability of 20% Ni—Ti alloy and can be used to infiltrate fine (10 micron) $Al_2O_3$ preforms.

3. A Process for Cermet Fabrication

The specific conditions utilized in the process of the invention for fabrication of the cermets of the invention are described above. The process thus comprises a selection of one or several blended ceramic powders of a specific particle sizes for fabrication of a presintered porous ceramic matrix. The metal or metal alloy to be used for a molten metal infiltration into a ceramic preform is than selected by matching the sintering temperature of the ceramic preform with the melting point and wetting characteristics of the metal or alloy.

In the case of aluminum oxide and titanium used for exemplarization of the process of the invention, a preformed matrix of 10 u diameter aluminum oxide particles that sinter above 1500° C. in one-half hour, as seen in FIG. 1, is infiltrated with a titanium alloy comprising 30% of weight % of nickel at 1400° C. in vacuum (10-6 torr). This infiltration is improved further by the addition of 0.5% sulfur to the aluminum oxide particles and by the addition of 10% silica to the 30% of Ni—Ti alloy (Table 1).

The cermets of the invention have a wide compositional range in that they can consist from about 5% to about 60% titanium or other metal. The range and amount of the metal effects its mechanical and physical properties. The moderate fracture toughness at low titanium contents (5%-30%) gives high wear resistance and low electrical conductivity for applications such as seal rings, brake shoes, corrosion resistant valve seats, etc. While density is increased with increasing titanium content, at these levels it is still attractive for armor applications due to low cost and multi-hit capability. When the metal content is increased above 25%, the properties shift to higher fracture toughness and possible electrical conductivity for such applications as bone replacement, for manufacturing MRI compatible surgical instruments and electrical contacts with moderate wear resistance. These and any other modifications of the process of the invention are intended to be within the scope of the invention.

The preferred system of the invention for preparation of cermets of the invention is the metal oxide system. The most preferred of the oxide systems are the aluminum oxide infiltrated with titanium, magnesium, lithium or their respective alloy.

The cermet of the invention is exemplarized and represented by the titanium-aluminum oxide system but other systems such as any combination of systems listed above is equally suitable for preparation of the cermets using the molten-metal-infiltration as long as the main premise of the invention, namely a use of a lower molten metal infiltration temperature than the sintering temperature of the ceramic powder, is present.

The procedure for fabrication of the new cermets described herein is suitable for screening and developing other cermet systems with promising properties specific to other applications not specifically described herein. All these variations and modifications are intended to be within the scope of this invention.

The composition of these cermets can be advantageously adjusted during fabrication by, for example, changing the proportions of ceramic/metal, changing the composition of the ceramic from a single material to a mixture of two or more materials, and changing the prefabrication conditions such as temperature, pressure and atmosphere.

In this invention, the obstacles previously encountered have been overcome by reducing the sinterability of the metal oxide and/or other systems, improving the wettability, and reducing the melting point of the metal used to infiltrate.

4. Cermets Suitable for Bone Replacement Implants

An additional advantage of this invention is that the cermets of the invention are conveniently fabricated from the components fully compatible with the human or mammal body and, having improved properties as described above, are therefore particularly suitable for fabrication of bone replacement implants. Currently, both alumina and titanium alloys are acceptable and FDA approved implant materials. These materials alone or in combinations, fabricated by methods known in the art do not possess the desired properties required for bond or joints replacement. However, because of the new processing, the cermets of the invention made of these two materials have similar properties as bones or joints to be replaced and have, in addition to other already listed properties, also an elasticity modulus and surface finish which prevents wear in the joint area and allows an attachment of the ligaments or other tissues.

The cermets according to the invention are composed of a high packing density porous ceramic matrix with evenly distributed ceramic particles presintered together and uniformly infiltrated with the molten metal. The density and porosity of the ceramic matrix is designed based on the intended use of the cermet. In case of bone implant, both the density and porosity of the cermet implant is similar to the porosity and density of the bone to be replaced.

Typically, for a custom-fit implant which needs to be shaped and finished during surgery, a porous prefabricate of the ceramic powder, preferably aluminum oxide, is prepared in near-net shape of the bone or joint before the operation. The method of the invention allows surgeons, within a typical implant operating time, to fit a specific bone replacement application, i.e. to fit the recipient's bones or joints, before the infiltration of the matrix with molten metal. Final shaping using machining, grinding, polishing and surface finishing is then done under the surgeon's instruction. The ceramic prefabricate can be modified to allow attachment of the ligament or tissue, to prevent such attachment, or to allow or disallow the joint lubrication. The surface of the prefabricate can also be modified in various regions to improve its wear resistance as a moving joint surface, its lubrication ability in a joint surface and surface condition to improve tissue attachment. Only after the implant has the shape that fits the patient, the molten metal, preferably titanium alloy, is infiltrated into the porous aluminum oxide ceramic pre-fabricate.

After the metal alloy infiltration, the surface of the cermet bone implant can additionally and optionally be modified to improve tissue attachment by, for example, removing the metal alloy at the surface and expose only porous aluminum oxide in regions where tissue attachment or bone growth is desired. Similarly, the implant surface can be modified for improved hardness by exposing that surface to a number of processes that harden the metal alloy like nitrating, ion-implantation, coating, etc. Areas that require self-lubrication for joint movement can be modified to have fine pores at the surface to allow body lubricates to flow into the joint region by removing the surface metal alloy after infiltration. When alternate lubricants are developed and/or used, these artificial lubricants are advantageously injected into these porous networks to lubricate moving parts.

The current invention provides a method utilizing these and/or other physiologically acceptable ceramics and metals to provide a cermet material that has the properties similar to bone than any other material known and available today.

Another equally important requirement for the acceptable bone or joint replacement materials is that they need to be magnetic resonance (MR) compatible. The magnetic resonance compatibility requires that the implants, instruments and tools used during the operation must be non-magnetic so that the implants, tools and instruments being used near or in the magnetic field will not be attracted to the magnets. These implants, instruments and tools must not effect the image of the magnetic resonance image (MRI) so as to give false views. The cermet materials of the invention are not magnetic and, therefore, meet the requirement for magnetic resonance compatibility. The degree of MRI compatibility depends on the amount and effect any metal component in the cermet will have on the image. Fine dispersing of non-magnetic metals like Ti in an $Al_2O_3$ matrix are MRI compatible at 25% Ti. Cermets are tested up to 5 Tesla in MRI units to determine their compatibility.

Utility

The cermets of the current invention are new materials having new and improved properties. These materials are suitable for manufacturing products having specific requirements as to their durability, toughness, fragility, brittleness, etc. They are particularly suitable for implants as bone and joint replacements.

The invention further provides options to customize the cermet to fit its intended use.

In addition to the cermets used as bone and joint replacements, the new cermets are suitable for fabrication of armors for military applications due to increased hardness, strength, and toughness. They have many advantages over cermets previously known and over ceramics or metals alone. They have also shown great potential as wear parts, cutting tools, surgical instruments and engine components in civil or military applications.

EXAMPLE 1

Preparation of Presintered Aluminum Oxide Matrix

This example describes the first step of the current method for preparation and testing of presintered aluminum oxide porous matrix. This procedure is suitable for determination of the optimal sintering temperature of the ceramic powder and for selection of its optimal particle size.

Five grams of aluminum oxide powder having particles sizes 0.2 µ, 1 µ, 5 µ, 10 µ, 20 µ, 50 µ, and 60 µ each were packed into preform shapes and cold pressed at 15,000 psi for 1 minute at room temperature to form a packed compact of the ceramic powder. Each compact was submitted to an increasing temperature inside a tungsten element furnace from 1200° C. up to 1700° C., under vacuum. The temperature was incrementally increased each 30 minutes by 200° C. under $10^{-6}$ torr pressure. The density of each compact was measured and its sintering temperature was noted from the onset of shrinkage. The preferred compacts had about 40% porosity and 60% density. The degree of sintering was determined for each particle size.

At higher particle sizes, the temperatures needed for sintering were much higher than temperatures needed for sintering of powders having smaller particle sizes. The results are seen in FIG. 1.

After determination of sintering temperature for each size was performed, each compact of different particle size was infiltrated with a molten titanium alloy in order to find out the best and most practical particle size of aluminum oxide powder to achieve even distribution of titanium. Compacts made of 0, 2 µ, 1 and 5 µ were found to have too high a density to permit a thorough infiltration with the molten metal. Compacts made of particle sizes higher than 60 µ required high sintering temperatures but were relatively large grain size.

Molten metal infiltration of compacts made of 10-50 µ particle sizes were found to be suitable for molten infiltration, having a sintering temperature between 1500° C. for 10 µ particles, 1600° C. temperature for 20 µ particles and 1660° C. for 50 µ particles. The most preferred was 10 µ particles compact having the right porosity and density allowing even and continuous molten-metal-infiltration with a titanium alloy (Ti—Ni 30%).

Other ceramic powders, namely aluminum nitride, aluminum boride, aluminum silicate, zirconium oxide, zirconium nitride, zirconium boride, zirconium silicate, hafnium oxide, hafnium nitride, hafnium boride, hafnium silicate, beryllium oxide, beryllium nitride, beryllium boride, beryllium silicate, vanadium oxide, vanadium nitride, vanadium boride, vanadium silicate, and other such compounds are treated according to the procedure described above, their individual sintering temperatures are determined for compacts of powder having different particle sizes.

EXAMPLE 2

Determination of Wettability of Titanium

This example illustrates a procedure used to determine wettability and wetting angle of titanium infiltration into aluminum oxide ceramic compacts in order to select conditions for molten-metal-infiltration. This procedure suitable for determination of the optimal wettability and wetting angle of the infiltrating metal or metal alloy.

The ceramic compact obtained in Example 1 was covered with a titanium-nickel alloy containing 20% or 30% of nickel. The ceramic metal composite was heated from 800° C. to 1600° C. in a vacuum under $10^{-6}$ torr. The temperature was selected on the basis of the sintering temperature of the ceramic powder composite. As the sintering temperature of aluminum oxide 10 μ particle size compact was found to be around 1500° C. and the sintering temperature of aluminum oxide 50 μ particle size compact was around 1660° C., the temperature of the molten titanium containing alloys was investigated so that only the alloys having the melting point below the sintering temperature were used.

The angle where ceramic/metal bonding was maximized was achieved with 30% titanium nickel alloy at temperature 1600° C. but the wetting angle near to zero was achieved at 1500° C. temperature. This alloy therefore was suitable for molten-metal-infiltration of aluminum oxide compact made of 10 μ particles and also for compact made of larger than 10 μ particle size.

The 20% titanium nickel alloy has about a 40 degree wetting angle at 1600° C. and it was found to be acceptable for metal infiltration of compacts made of smaller or equal to 50 μ particles. At 1500° C. this alloy had about a 70 degree wetting angle and it would not be very suitable for metal infiltration of compacts made of about 10 μ particles.

The results discussed herein are seen in FIG. 2.

In this manner, wetting properties of other metals such as magnesium, nickel, aluminum, calcium, lithium or their alloys in any combination, are investigated in the same manner and a determination is made of the most suitable paring of the ceramic powder compact and the metal or metal alloy used for molten-metal-infiltration.

EXAMPLE 3

Process for Fabrication of Cermets

This example illustrates a process for fabrication of cermets of the invention having properties suitable to be used as bone implants.

The presintered aluminum oxide compact of 10 μ particle sizes of Example 1 is cast into the bone near shape form and pressed together. The compact is than presintered at 1500° C. in the furnace heated in incremental increased temperatures for 30 minutes. The presintered porous ceramic matrix is brought in contact with the melted titanium-nickel 30% alloy at a temperature of around 1400 or 1450° C., which temperature is lower than the sintering temperature of the aluminum oxide. The contact is made in the vacuum furnace at $10^{-6}$ torr pressure for about 10 minutes. Titanium-nickel 30% alloy infiltrated uniformly into the ceramic matrix and good ceramic/metal interfacial bonding was achieved.

The bone implant was then submitted to testing for strength, fragility, brittleness and its metal infiltration was microscopically checked. There were no void or metal accumulation and the metal infiltration was even and uniform throughout the whole cermet structure.

What is claimed is:

1. A process for fabrication of cermets comprising of a ceramic powder infiltrated with a molten metal or metal alloy, said process comprising:
    (a) producing a ceramic preform matrix of a desired shape having a porosity from 30% to less than 50% by presintering a predetermined ceramic powder, said ceramic powder further comprising particles of the same sizes from greater than 10μ to about 50μ and selected from the group consisting of any one or a mixture of aluminum oxide, aluminum nitride, aluminum boride, aluminum silicate, hafnium oxide, hafnium nitride, hafnium boride, hafnium silicate, vanadium oxide, vanadium nitride, vanadium boride, vanadium silicate, beryllium oxide, beryllium nitride, beryllium borate and beryllium silicate, said particle sizes and said group selected in combination so that said particles remain of the same size following presintering; and
    (b) molten metal infiltrating said ceramic preform matrix of step (a) with a metal selected from the group consisting of titanium, nickel, magnesium, calcium, aluminum, lithium, copper, iron, silicon, manganese, cobalt, molybdenum, niobium, zirconium, and their combination wherein said selected metal has a melting point lower than a presintering temperature of said ceramic powder of step (a) to enable a molten metal or a molten metal alloy infiltration into said ceramic preform matrix at a temperature lower than said presintering temperature.

2. The process of claim 1 wherein additionally a wetting angle of the metal or metal alloy is determined before said ceramic preform matrix produced by step (a) is infiltrated.

3. The process of claim 2 wherein said wetting angle for said metal and said ceramic preform matrix interaction is zero or is not larger than about 60 degrees.

4. The process of claim 3 wherein said ceramic powder includes presintering under vacuum.

5. The process of claim 4 wherein said molten metal is infiltrated evenly into said presintered ceramic preform matrix.

6. The process of claim 1, wherein said presintering temperature is between 1400° C. and 1660° C.

7. The process of claim 1, wherein said aluminum oxide has particle sizes about 10μ.

8. The process of 1, wherein said presintering temperature is about 1500° C.

9. The process of claim 1, wherein said metal used for molten-metal-infiltration includes a titanium alloy.

10. The process of claim 9 wherein said metal is selected from the group of binary, ternary and quaternary alloy shown in Table 1.

11. The process of claim 9 wherein said titanium alloy contains about 20-30% of nickel.

12. The process of claim 11 wherein the temperature for molten-metal-infiltration is under 1500° C.

13. The process of claim 12 wherein said ceramic powder additionally contains an additive selected for the group consisting of calcium oxide, magnesium oxide and sulfur present in an amount for about 0.01 to about 1%.

* * * * *